(12) United States Patent
Zoumalan

(10) Patent No.: US 10,835,125 B1
(45) Date of Patent: Nov. 17, 2020

(54) DEVICE FOR MEASURING FACIAL ANATOMICAL PARAMETERS

(71) Applicant: Christopher Zoumalan, Beverly Hills, CA (US)

(72) Inventor: Christopher Zoumalan, Beverly Hills, CA (US)

( * ) Notice: Subject to any disclaimer, the term of this patent is extended or adjusted under 35 U.S.C. 154(b) by 0 days.

(21) Appl. No.: 16/903,482

(22) Filed: Jun. 17, 2020

(51) Int. Cl.
  *A61B 5/00* (2006.01)
  *A61B 3/00* (2006.01)
  *A61B 5/107* (2006.01)
  *A61B 90/00* (2016.01)
  *A61B 3/11* (2006.01)

(52) U.S. Cl.
  CPC .......... *A61B 5/0079* (2013.01); *A61B 3/0075* (2013.01); *A61B 3/0083* (2013.01); *A61B 3/111* (2013.01); *A61B 5/107* (2013.01); *A61B 5/1072* (2013.01); *A61B 2090/061* (2016.02)

(58) Field of Classification Search
  CPC ..... A61B 5/0079; A61B 5/107; A61B 5/1072; A61B 3/0075; A61B 3/0083; A61B 3/111; A61B 2090/061
  See application file for complete search history.

(56) References Cited

U.S. PATENT DOCUMENTS

| | | | |
|---|---|---|---|
| 2,043,230 A * | 6/1936 | Boll | A61B 3/111 33/512 |
| 2,107,534 A | 2/1938 | Houser | |
| 5,005,966 A | 4/1991 | Handler | |
| D345,929 S | 4/1994 | Naugle, Jr. | |
| 5,379,079 A * | 1/1995 | Kratky | A61B 3/0075 351/204 |
| 7,384,147 B1 * | 6/2008 | Ameri | A61B 3/00 351/200 |
| 7,699,607 B2 | 4/2010 | Margossian | |
| 8,931,182 B2 | 1/2015 | Raab et al. | |

OTHER PUBLICATIONS

Machine Translation of CN 108392171 (Year: 2018).*
Machine Translation of CN 102475536 (Year: 2013).*

* cited by examiner

*Primary Examiner* — Devin B Henson
(74) *Attorney, Agent, or Firm* — Eandi Fitzpatrick LLP; William Fitzpatrick

(57) ABSTRACT

A device for measuring facial anatomical parameters is provided. The device has a vertical bar having a top portion, middle portion, and a bottom portion and a horizontal slide adjustably affixed to the vertical bar. It has a forehead positioner pivotably and adjustably affixed to the top portion of the vertical bar, wherein the forehead positioner receives a forehead of the patient, a first mirror adjustably affixed to the left portion of the horizontal slide, wherein the first mirror is slidable along the horizontal slide, and wherein the first mirror rotates around its own Y-axis, and a second mirror adjustably affixed to the right portion of the horizontal slide, wherein the second mirror is slidable along the horizontal slide. A measuring grid on or proximate both the first mirror and the second mirror, wherein the measuring grids allows an examiner to accurately measure a point of interest of the facial anatomic parameters.

20 Claims, 9 Drawing Sheets

DEVICE FOR MEASURING FACIAL ANATOMICAL PARAMETERS

FIELD OF THE INVENTION

The present invention generally relates to a device for measuring facial anatomical parameters. More specifically, the present invention relates to a device that enables an Examiner to accurately measure facial anatomical parameters thereby assessing facial symmetry before and after an aesthetic or surgical treatment.

BACKGROUND

Measurement of facial anatomical parameters is often needed for rhinoplastic, facial, oculoplastic, orbital, dental, plastic reconstructive repair, and aesthetic surgical and nonsurgical procedures. By measuring facial parameters of critical importance, the physician or surgeon can accurately evaluate the condition of the patient. Measurement of facial anatomical parameters before and after a procedure (i.e., surgery or a nonsurgical procedure) also provides a way of assessing results of the surgery. The measurement process can be often difficult and tedious due to accuracy requirements and the anatomical shape of the face.

Currently, there are different systems and methods are available to measure facial anatomical parameters. Manual anthropometry is one of the methods to make surface measurements using sliding and spreading calipers and a flexible measuring tape. The technique is accessible due to low-cost but has major drawbacks due to excessive time involved in taking measurement and the fact that during measurement the tools distorts the soft tissue and, further, errors are introduced to measurements.

Manual anthropometry makes surface measurements using sliding and spreading calipers and flexible measuring tape. In addition, the measurement of facial anatomical parameters could be used for assessing facial symmetry. Most of the existing approaches for face symmetrization are achieved by measuring the facial anatomical parameters based on the facial landmark extractions. However, the accuracy of those extracted landmarks could drop dramatically under certain circumstances, for example, the variations in the head poses, illuminations, occlusions and many other aspects.

As an example, U.S. Pat. No. 5,379,079 to Vladimir Kratky discloses an attachment device for an exophthalmometer to measure exophthalmos in a patient. A horizontal bar is used for the movement in an anterior-posterior direction perpendicular to the face of the patient, and the vertical planes on either side of the nasion-engaging member of arcuate arms for engaging the forehead. The measurement of exophthalmos is done by using the exophthalmometer i.e. in the case of a Hertel® exophthalmometer. The device is combined with a shaft portion of two movable spaced apart carrier portions, and a mirror inclined to reflect the calibrate scale in which corneal apex of the patient eye is superimposed on the calibrate scale. The exophthalmos is measured before and after a procedure which affects the orbit such as orbitotomy to remove an orbital mass.

Another example is shown in U.S. Pat. No. 7,699,607 to Margossian, which discloses a facial anatomical parameter locating and measuring device to view and locate the face of patient's parameter for evaluation of the aesthetic harmony. The bi-pupillary lines are horizontal which slide perpendicularly on the frame and mounted on the uprights of the frame. A pad in the device is triangular/rectangular in shape, and frame is perpendicular to the vertical uprights which slide/aligned with the bi-pupillary line of the patient. The position of the frame is adjusted in relation to the face of the patient by pivoting and sliding the frame on the lower cross-member. The asymmetries of the patient face and/or jaw are measured, and the small length is compared with the yokes in the dental field.

However, the existing devices do not measure all required features of facial anatomy and in some cases lack the required accuracy to measure the facial anatomical parameters before or after an aesthetic or surgical treatment.

In light of the above-mentioned problems, there is a need for a device used for accurately measuring facial anatomical parameters, thereby assessing facial symmetry before and after an aesthetic or surgical treatment.

SUMMARY OF THE INVENTION

The present invention generally discloses a device for measuring facial anatomical parameters. Further, the present invention discloses a device configured to enable an Examiner to accurately measure facial anatomical parameters, thereby assessing facial symmetry before and after an aesthetic or surgical treatment. The measurements of the facial anatomical parameters are often needed for rhinoplastic, facial, oculoplastic, orbital, dental, plastic reconstructive repair, and aesthetic surgical procedures.

In one embodiment, the device enables the Examiner (e.g., Physician, nurse, technician, surgeon and the like) to securely and adjustably position on the patient's face for precisely measuring facial anatomical parameters. In one embodiment, the device enables the Examiner to measure facial anatomical parameters, thereby assessing facial symmetry before and after an aesthetic or surgical treatment. The device measures the anterior, superior, and inferior and posterior displacement of specific facial anatomic parameter of interest, i.e. the temples, cheeks, globe position, mid-face, nose, jaw, chin, lips, and other parts of the face.

In one embodiment, the device comprises a frame having a vertical bar having a top portion, bottom portion and middle portion, and a horizontal slide (or slide rule). In one embodiment, the horizontal slide is securely and adjustably affixed to the vertical bar using a bracket or a connector and a latching member or knob. The horizontal slide of the frame comprises a calibration scale, for example, millimeter notches that designate the distance from the midline. In one embodiment, the device further comprises a pair of triangular prisms or mirrors, a forehead positioner, a stereoscopic viewer with a pair of eye pieces or elongated tube members, and a chin bracket. In one embodiment, the forehead positioner is pivotably and adjustably affixed to a top portion of the vertical bar. The forehead positioner moves anteriorly and posteriorly via an adjustable slide and also moves up and down via a hinge. The forehead positioner is a rigid semicircular to fit around the patient's forehead. The elongated tube members comprise two strings or other material that make a cross at the end of each tube. To remain in midline, the Examiner needs to see both of these cross strings in both tubes to remain in midline during the measurement.

In one embodiment, the mirrors are adjustably affixed to both sides of the horizontal slide using an adjustable member and a rotating element on each side. In one embodiment, the rotating elements on each side enable the Examiner to adjust the mirrors using the adjustable members depending upon the part of the face measuring, for example, patient's nose or cheek. In one embodiment, the adjustable members on each side are provided with etched (e.g., laser etched, stickers) X/Y axis with millimeter notches on them so the points on the face correspond to certain portion on the mirror, thereby determining facial symmetry. In operation, the points on the mirrors should be the same if there is symmetry between the two sides of the face. If there is one side that is asymmetric or depressed by 3 mm, the mirror will show that one side is back by 3 mm relative to the other mirror. In one embodiment, the adjustable members on each side comprise mirror mounts and mirror slides, respectively.

In one embodiment, the stereoscopic viewer is movably affixed to the vertical bar using the knob. The stereoscopic viewer moves up and down by adjusting the knob and is locked in by the knob. In one embodiment, the pair of eye pieces are adjustably and slidably connected to the stereoscopic viewer to allow for the appropriate interpupillary distance for the examiner. The stereoscopic viewer is used to confirm that the examiner's facial position remains in the midline to ensure the measurements are accurate. Optionally, a measurement telescopic pen that makes contact with the knob and the examiner's nose may be included to further ensure that the examiner's facial position remains in midline.

In one embodiment, the chin bracket is adjustably affixed to a lower portion of the vertical bar via a support arm using a knob. The support arm is movably connected to the vertical bar using an adjustable bracket and a knob. In one embodiment, the device further comprises a handle, which is securely affixed to the bottom portion of the device. In one embodiment, the enables the Examiner to conveniently adjust the device as straight as possible for accurately measuring superior, inferior, posterior and anterior displacement of facial anatomic parameters. The handle provides sufficient grip for the Examiner to securely hold the device during use. Optionally, the handle is adjustably fixed to an object such as a chair or patient bed, or the patient can hold on to it during the examination.

In embodiments, a device for measuring facial anatomical parameters comprises vertical bar having a top portion, middle portion, and a bottom portion, a horizontal slide adjustably affixed to the vertical bar, wherein the horizontal slide is shaped as an arc having a left portion and a right portion, and wherein the horizontal slide is dimensioned for a face of a patient, a forehead positioner pivotably and adjustably affixed to the top portion of the vertical bar, wherein the forehead positioner receives a forehead of the patient, a first mirror adjustably affixed to the left portion of the horizontal slide, wherein the first mirror is slidable along the horizontal slide, and wherein the first mirror rotates around its own Y-axis, a second mirror adjustably affixed to the right portion of the horizontal slide, wherein the second mirror is slidable along the horizontal slide, and wherein the first mirror rotates around its own Y-axis, and a measuring grid on or proximate both the first mirror and the second mirror, wherein the measuring grids allows an examiner to accurately measure a point of interest of the facial anatomic parameters.

In embodiments, a method for measuring facial anatomical parameters is provided. The method comprises marking anatomical areas of interest of the facial anatomical parameters, positioning a vertical bar having a top portion, middle portion, and a bottom portion proximate the face of a patient, wherein a horizontal slide is adjustably to the vertical bar, and wherein the horizontal slide is shaped as an arc having a left portion and a right portion, positioning a patient's forehead in a forehead positioner, wherein the forehead positioner is pivotably and adjustably affixed to the top portion of the vertical bar, adjusting a first mirror to ensure the anatomical areas of interest on the patient's face is visible in the first mirror, adjusting a second mirror to ensure sure the anatomical areas of interest on the patient's face is visible in the second mirror, wherein each of the first and second mirrors are adjustably affixed to the horizontal slide, wherein each of the first and second mirror is slidable along the horizontal slide, and wherein each of the first and second mirror rotates around its own Y-axis, and taking measurements of the anatomical area of interest.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

Figure 1:
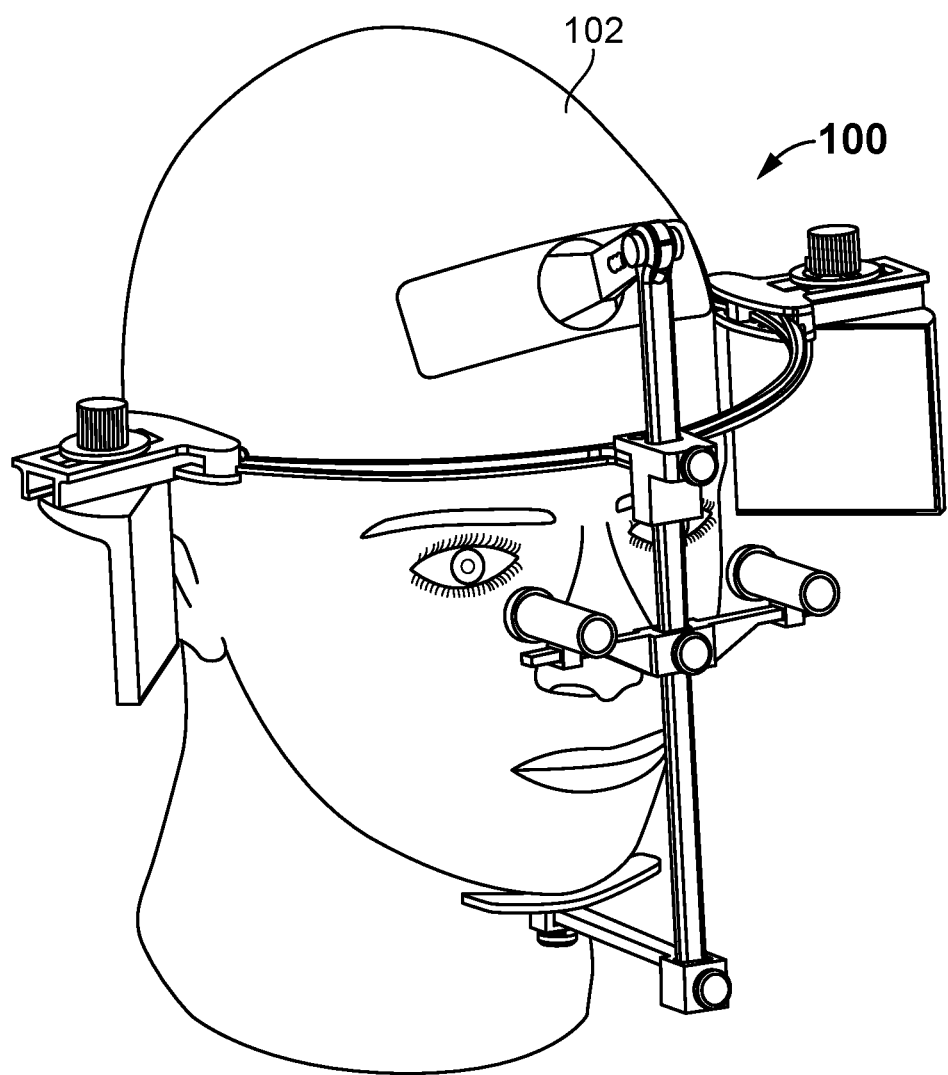
FIG. 1 shows a perspective view of a device securely positioned on a patient's face for measuring facial anatomical parameters in an embodiment of the present invention.

The present invention is best understood by reference to the detailed figures and description set forth herein.

Embodiments of the system are discussed below with reference to the examples. However, those skilled in the art will readily appreciate that the detailed description given herein with respect to these examples is for explanatory purposes as the system extends beyond these limited embodiments. For example, it should be appreciated that those skilled in the art will, in light of the teachings of the present system, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the system that are too numerous to be listed but that all fit within the scope of the system. Also, singular words should be read as plural and vice versa and masculine as feminine and vice versa, where appropriate, and alternative embodiments do not necessarily imply that the two are mutually exclusive.

It is to be further understood that the present system is not limited to the particular methodology, compounds, materials, manufacturing techniques, uses, and applications, described herein, as these may vary. It is also to be understood that the terminology used herein is used for the purpose of describing particular embodiments only and is not intended to limit the scope of the present system. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this system belongs. Preferred methods, techniques, devices, and materials are described, although any methods, techniques, devices, or materials similar or equivalent to those described herein may be used in the practice or testing of the present system.

The present system discloses a device that enables an Examiner to accurately measure facial anatomical parameters thereby assessing facial symmetry before and after an aesthetic or surgical treatment.

Referring to FIG. 1, a device 100 securely positioned on a patient's face 102 for measuring facial anatomical parameters is disclosed. In one embodiment, the device 100 is enables the Examiner to securely and adjustably position on the patient's face 102 for precisely measuring the facial anatomical parameters. In one embodiment, the device 100 is further configured to enable an Examiner or a physician to measure facial anatomical parameters, thereby assessing facial symmetry before and after an aesthetic or surgical treatment. The device 100 measures the anterior, posterior, superior, and inferior displacement of specific facial anatomic parameter of interest, i.e. the temples, cheeks, globe position, mid-face, nose, jaw, chin, lips, and other parts of the face.

Figure 2:
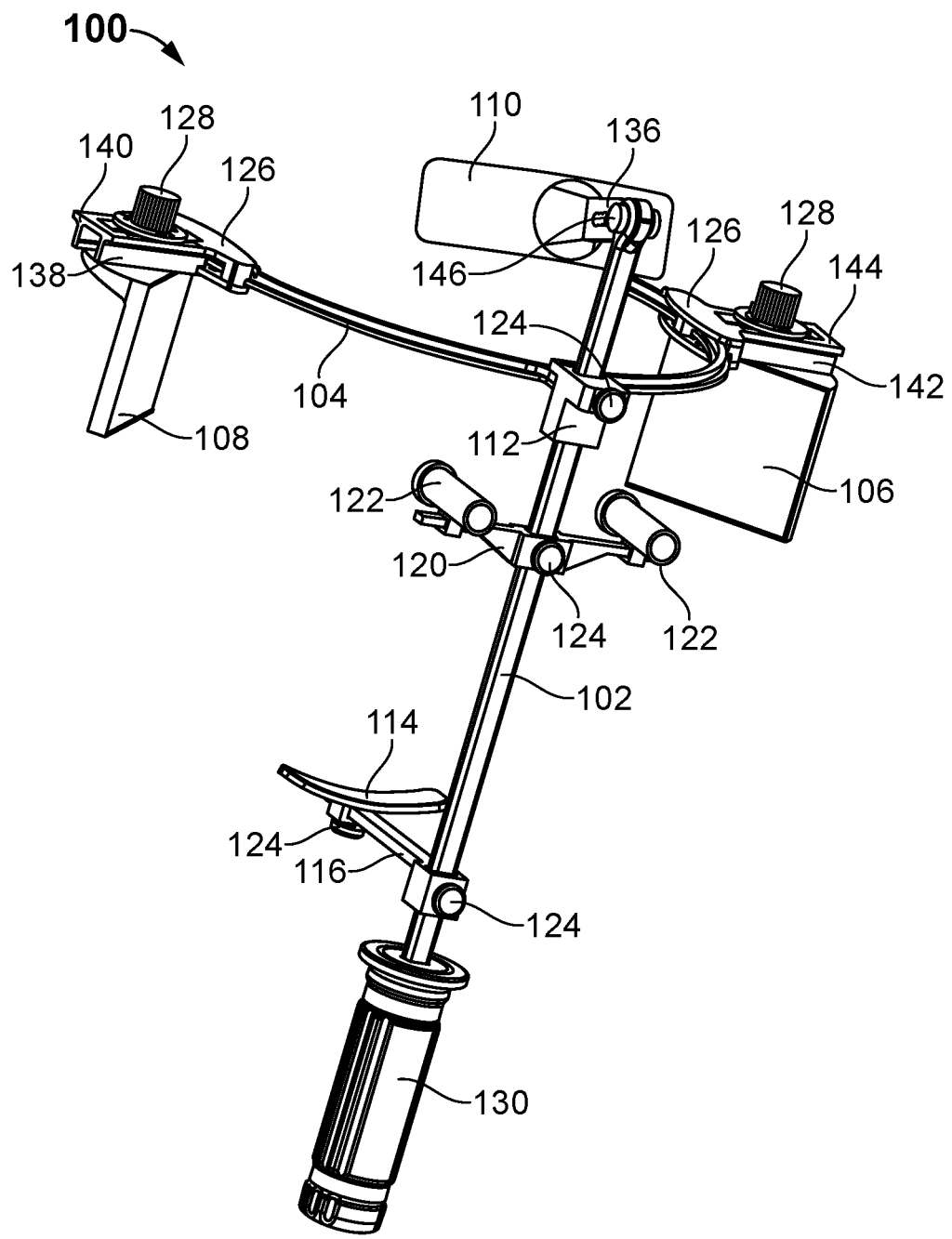
FIG. 2 shows a perspective view of the device used for measuring facial anatomical parameters in one embodiment of the present invention.
Figure 3:
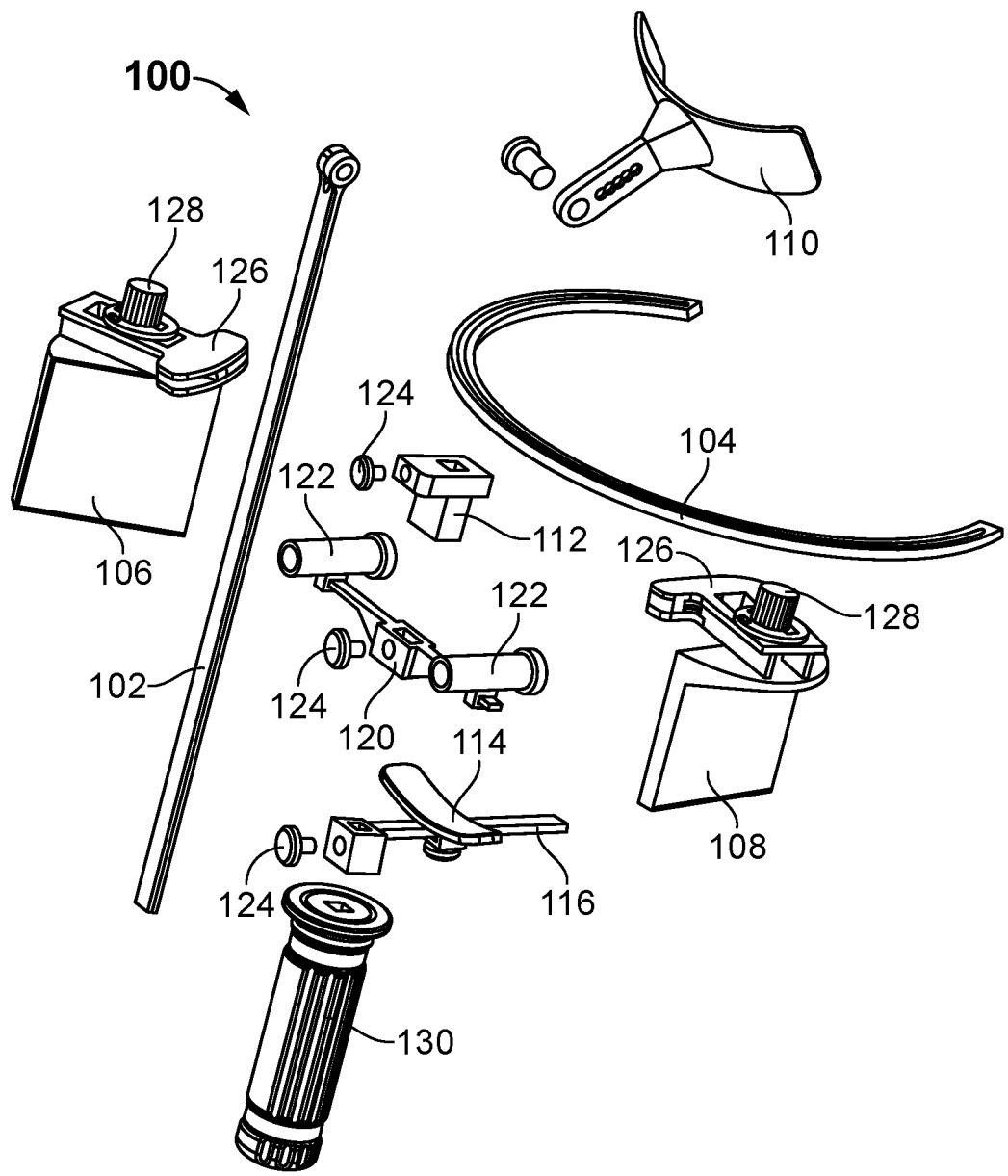
FIG. 3 shows an exploded view of the device used for measuring facial anatomical parameters in one embodiment of the present invention.

Referring to FIGS. 2 and 3, the device 100 for measuring facial anatomical parameters is in perspective view and exploded view, of the device used for measuring facial anatomical parameters in one embodiment of the present invention.

Figure 8:
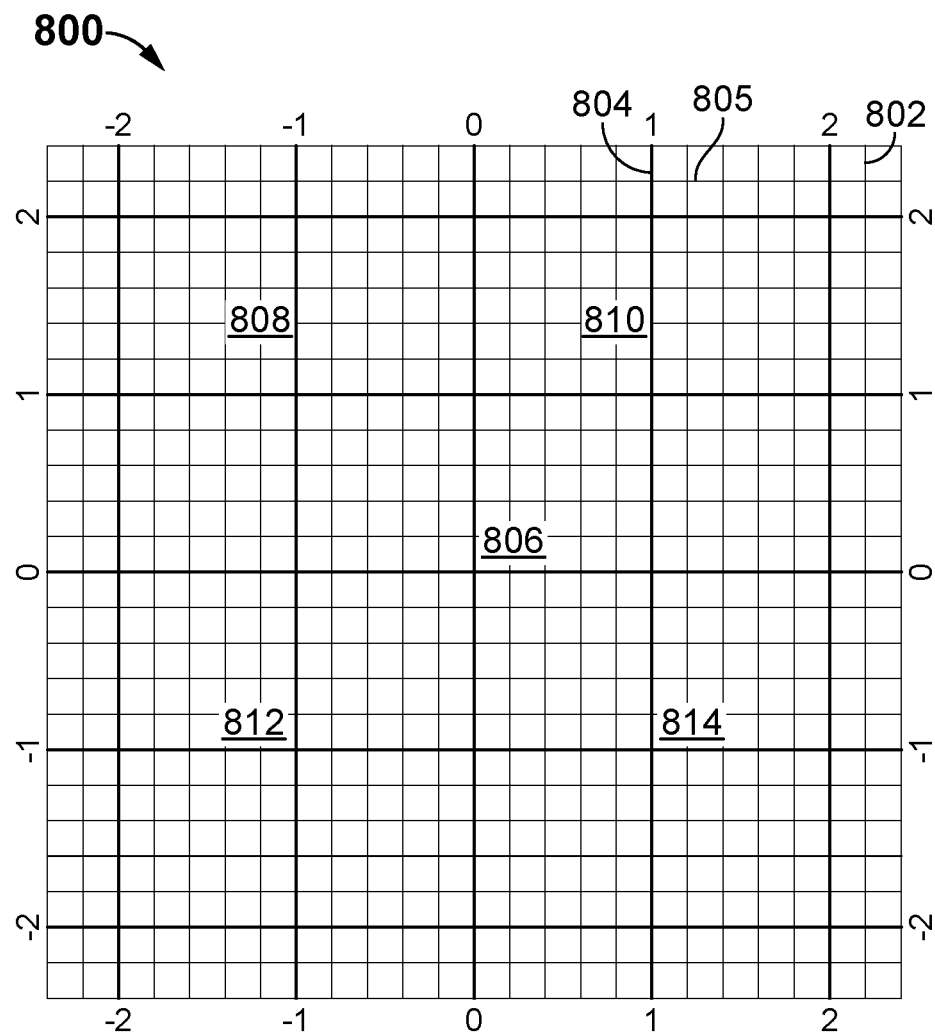
FIG. 8 is front view of a mirror that may be used in embodiments of the present invention.

In one embodiment, the device 100 comprises a frame having a vertical bar 102 and a horizontal slide or slide rule 104. The vertical bar is sized at around thirty percent longer than a person's face and can be either held by the Examiner or locked into a static base (e.g., attached to a chair. In one embodiment, the horizontal slide 104 is securely and adjustably affixed to the vertical bar 102 using a bracket or a connector 112 and a latching member or knob 124. In operation, the slide 104 fits around the patient's head. In one embodiment, the horizontal slide 104 of the frame comprises a calibration or measuring scale, for example, millimeter notches that designate the distance from the midline where they both meet at the connector 112. In one embodiment, the device 100 further comprises a pair of triangular prisms or mirrors (106 and 108) having etched millimeter marks on each (as shown in FIG. 8) a forehead positioner 110, a stereoscopic viewer 120 with a pair of eye pieces 122 which are elongated tube members, and a chin bracket 114.

The forehead positioner 110 is pivotably and adjustably affixed to a top portion of the vertical bar 102. The forehead positioner 110 moves anteriorly and posteriorly via an adjustable slide 136 and also moves up and down via a hinge 146 (e.g., four axes of movement). The forehead positioner 110 is a rigid semicircular to fit around the patient's head.

In one embodiment, the mirrors (106 and 108) are configured to adjustably affix to both sides of the horizontal slide 104 using an adjustable members (126 and 150) and a rotating element (128 and 152) on each side. In one embodiment, the rotating elements (128 and 152) on each side are configured to enable the Examiner to adjust the mirrors (106 and 108) using the adjustable members (126 and 150) depending upon the part of the face measuring, for example, the patient's nose or cheek. In this way, the mirrors 106 and 108 via adjustable members (126 and 150) and rotating element (128 and 152) move along the slide, rotate along its Y-Axis, and also further slide along adjustable member outward and inward via mirror slide (140 and 144). and In one embodiment, the adjustable members (126 and 150) on each side are provided with laser etched X/Y axis with millimeter notches on them so the points on the face correspond to certain points or portions on the mirror, thereby allowing the Examiner to view, measure and ultimately determine the face symmetry. Stickers may be used as well in some embodiments. The points on the mirrors (106 and 108) should be the same if the anatomical landmarks are symmetric. If there is one side that is asymmetric or depressed by 3 mm, the mirror will show that one side is back by 3 mm relative to the other mirror. In one embodiment, the adjustable members (126 and 150) on each side comprise mirror mounts (138 and 142) and mirror slides (140 and 144), respectively.

In one embodiment, the stereoscopic viewer 120 is movably affixed to the vertical bar 102 using stereoscopic knob 154, though other types of latches or locks may be used. In one embodiment, the stereoscopic viewer 120 is configured to move up and down by adjusting the stereoscopic knob 154. In one embodiment, the pair of eye pieces 122 are adjustably and slidably connected to the stereoscopic viewer 120 for measuring distance between the examiner's pupils. The examiner should see through both tubes during the examination to ensure the examiner is midline. Using the pair of eye pieces 122, the Examiner may remain in midline for the device to work. In operation, when measuring the right side of the patient's face, the Examiner will site using his or her right eye only, and when measuring the left side of the patient's face, the Examiner will use his/her left eye only. In operation, the elongated tube members comprise crosshairs 402 (e.g., two strings or threads) that make a cross at the end of each tube. To remain in midline, the Examiner must be able to see both of these in both tubes to remain in midline during the measurement phase. The stereoscopic knob 154 allows the Examiner to fix in midline position.

The stereoscopic viewer 120 does not perform measurements but rather acts as a calibrator to ensure the Examiner remains in the midline. Generally, Examiners will be ocular dominant and thus have a tendency of using the same eye to measure both mirrors, which may lead to inaccuracies. Consequently, as the Examiner is measuring features of the patient, using the stereoscopic viewer, the Examiner's right eye will be only used to measure from the right mirror, the left eye only for the left mirror, which leads to more accurate measurements. The stereoscopic viewer eye pieces are adjustable and are able to adjust for each Examiner's interpupillary distance.

In one embodiment, a measurement telescope pen may be included that The Examiner places to the Examiner's nose and the point around the stereoscopic knob 154 to ensure a reliable focal length between the Examiner and the patient. During measurement, the Examiner uses his/her right eye to measure right mirror, and left eye to measure left mirror, and must remain in midline as well.

In one embodiment, the chin bracket 114 is adjustably affixed to a lower portion of the vertical bar 102 via a support arm 116 using a chin bracket knob 156. The support arm 116 is movably connected to the vertical bar 102 using an adjustable bracket 118 and the chin bracket knob 156. In one embodiment, the device 100 further comprises a handle 130, which is securely affixed to the bottom portion of the device 100.

Figure 4:
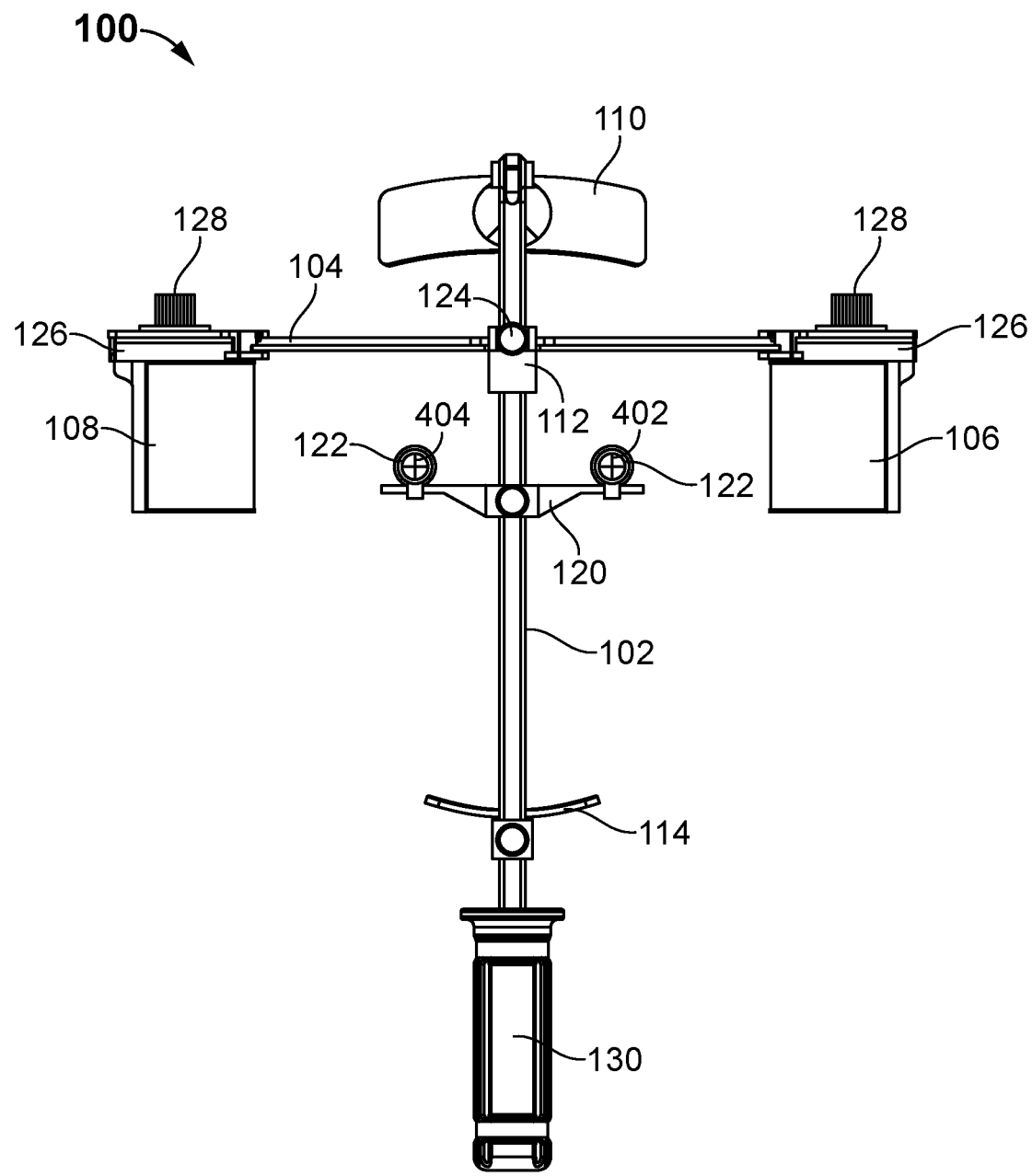
FIG. 4 shows a front view of the device used for measuring facial anatomical parameters in one embodiment of the present invention.
Figure 5:
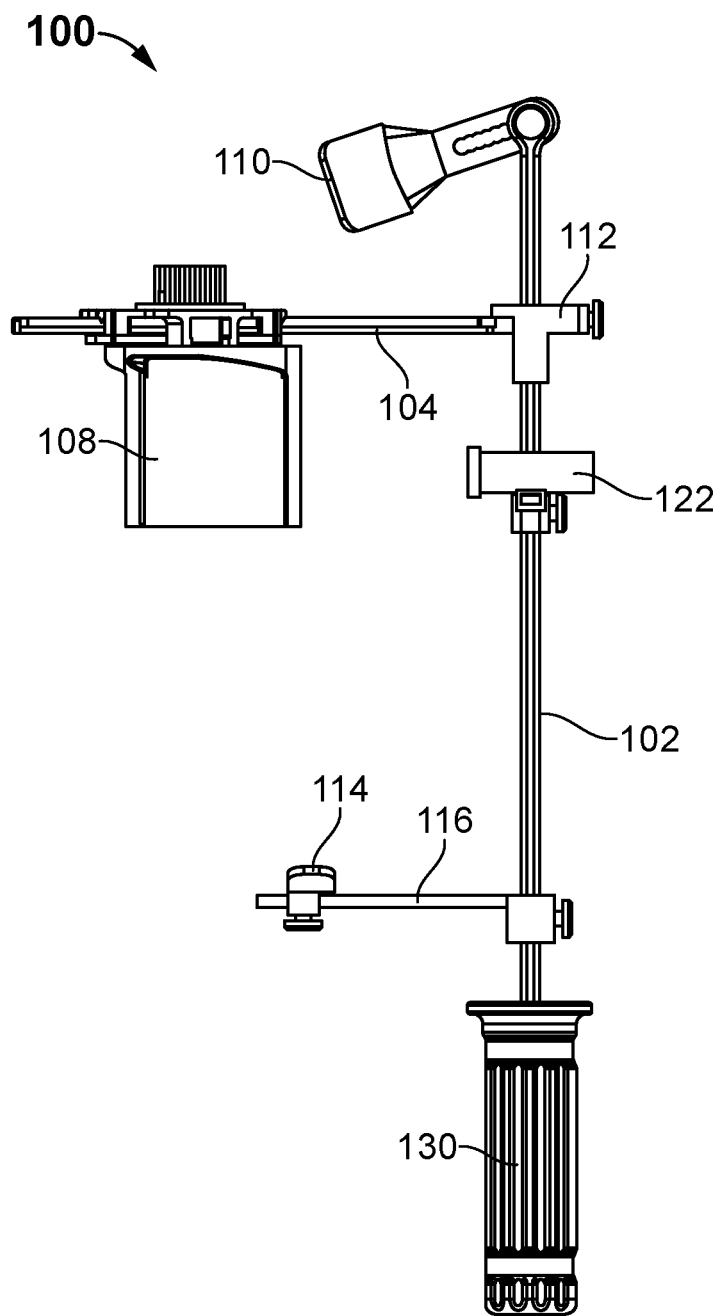
FIG. 5 shows a side view of the device used for measuring facial anatomical parameters in one embodiment of the present invention.

Referring now to FIGS. 4-5, the front view and side view of the device 100 in one embodiment is shown. In one embodiment, the horizontal slide 104 is configured to slidably move upwards and downwards along the vertical bar 102 by adjusting the bracket 112 and the knob (or any type of latching member) 124. In one embodiment, the knob 124 allows up and down to measure different parts of face from forehead down to chin and also allows the horizontal slide 104 to move up and down vertically, then be locked into appropriate position. In one embodiment, the forehead positioner 110 is configured to position on a patient's forehead comfortably. The forehead positioner 110 may be adjusted by the Examiner according to the patient's facial features. In one embodiment, the mirrors (106 and 108) are configured to precisely measure the width of the patient's face. The mirrors (106 and 108) are adjustably affix to both sides of the horizontal slide 104 using the adjustable members (126 and 150) and the rotating element (128 and 152) on each side. The mirrors 106 and 108 each have crosshatched millimeter etching as shown more clearly in FIG. 8.

In one embodiment, the pair of eye pieces 122 are adjustably affix to the stereoscopic viewer 120. In operation, the eye pieces comprise crosshairs 402 and 404 (e.g., two strings or threads) shown in FIG. 4 that make a cross at the end of each eye piece/tube. To remain in midline, the Examiner must be able to see both of these in both tubes to remain in midline during the measurement phase. The stereoscopic knob 154 allows the Examiner to fix in midline position.

In one embodiment, the chin bracket 114 is configured to adjustably position under the patient's chin to precisely measure the facial anatomical parameters. In an embodiment, the handle 130 enables the Examiner to conveniently adjust the device 100 as straight as possible for accurately measuring superior, inferior, posterior and anterior displacement of facial anatomic parameters. The examiner may hold the device, the patient may hold the device, or it may be attached to a static surface.

Figure 6:
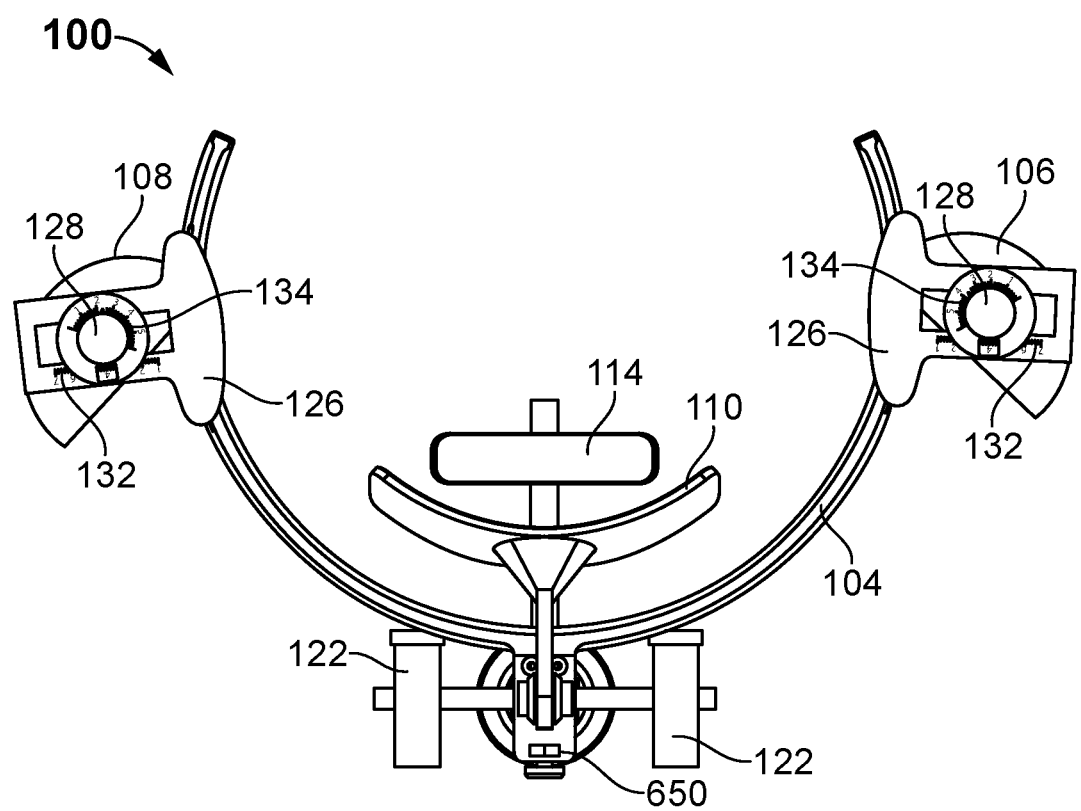
FIG. 6 shows a top view of the device used for measuring facial anatomical parameters in one embodiment of the present invention.

Referring to FIG. 6, the top view of the device 100 in one embodiment is disclosed. In one embodiment, the horizontal slide 104 of the frame having a calibrate scale to accurately measure the patient's facial width. In one embodiment, the horizontal slide 104 is shaped in, but not limited to, an arc that allows to rotate and adjust to fit in each patient's facial width. The calibrate scale on the horizontal slide 104 allows the Examiner to ensure the mirrors (106 and 108) equidistant from each other. Thus, measurements could be taken from all parts of face from nose to ear to see if one eye socket is more depressed than the other etc. In one embodiment, the rotating elements (128 and 152) on each side are configured to enable the Examiner to adjust the mirrors (106 and 108) using the adjustable members (126 and 150). In one embodiment, the adjustable members (126 and 150) on both sides comprises a calibrate scale 132 to precisely measure the width of the Patient's face. The mirrors (106 and 108) could be adjusted precisely and that they measure differing parts of the face that have different widths. In one embodiment, the device 100 further comprises a built-in level 650 to allow the Examiner to keep the device 100 as straight as possible for accurately measuring superior, inferior, posterior and anterior displacement of facial anatomic parameters. The mirrors (106 and 108) have a preprinted grid (e.g., 2 mm×2 mm grid boxes with having superior and inferior gridlines) as described in FIG. 8 to aid measurements.

Figure 7:
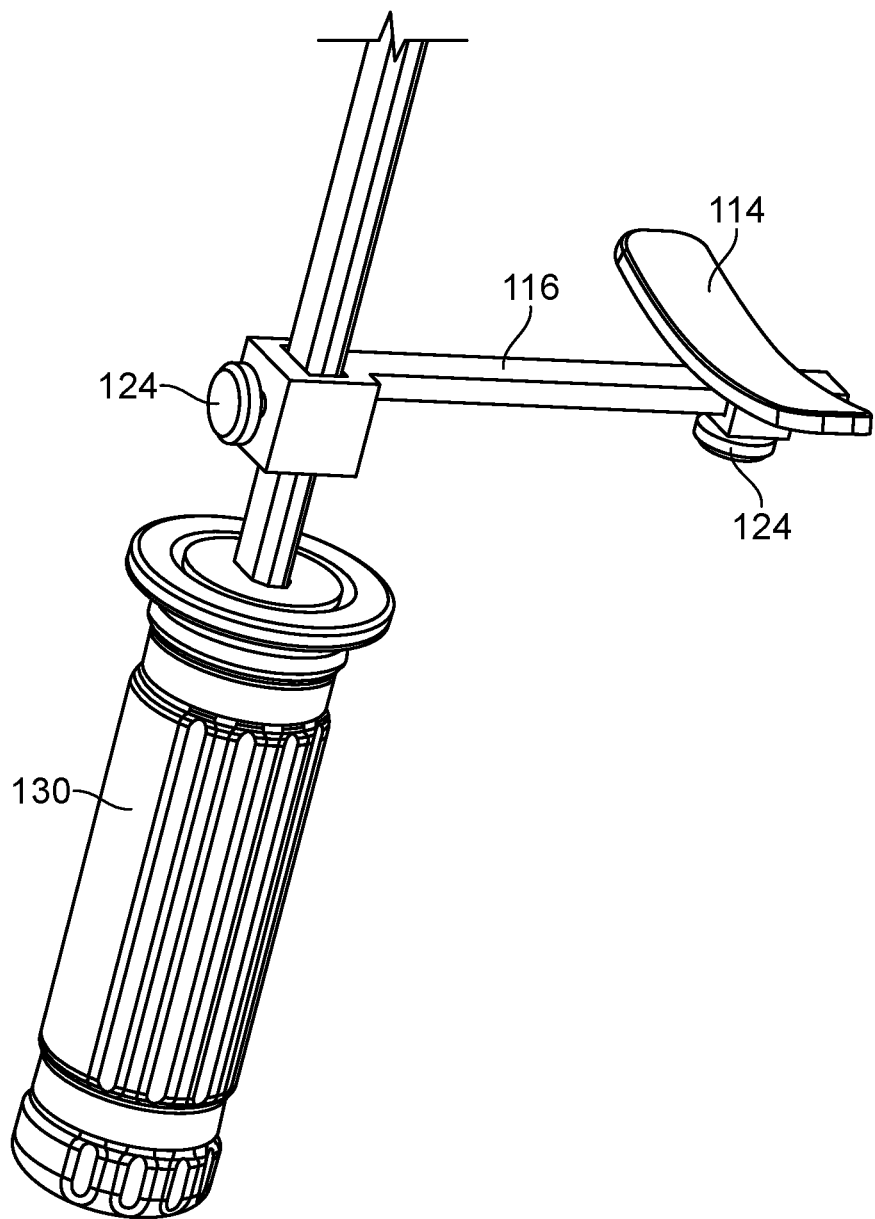
FIG. 7 shows a perspective view of a chin bracket and a handle of device in one embodiment of the present invention.

Referring to FIG. 7, the chin bracket 114 and the handle 130 of device 100 is disclosed. In one embodiment, the chin bracket 114 has an arc shape to precisely and conveniently position under the patient's chin for accurately measuring the facial anatomical parameters. In one embodiment, the handle 130 is configured to enable the Examiner to conveniently adjust the device 100 as straight as possible for accurately measuring superior, inferior, posterior and anterior displacement of facial anatomic parameters. The handle 130 provides sufficient grip for the Examiner to securely hold the device 100 during use.

Referring now to FIG. 8, exemplary mirrors 106 and 108 are shown generally at 800. The face of the mirror may comprise grids 802 having major and minor axis 804 and 805. The mirrors have a middle of the X and Y axis 806 and four quadrants: 808, 810, 812, and 814. The measurements may be laser etched or a sticker supplied on the mirror (or drawn on) and scaled at millimeters, from −2 mm through +2 mm for example.

Figure 9:
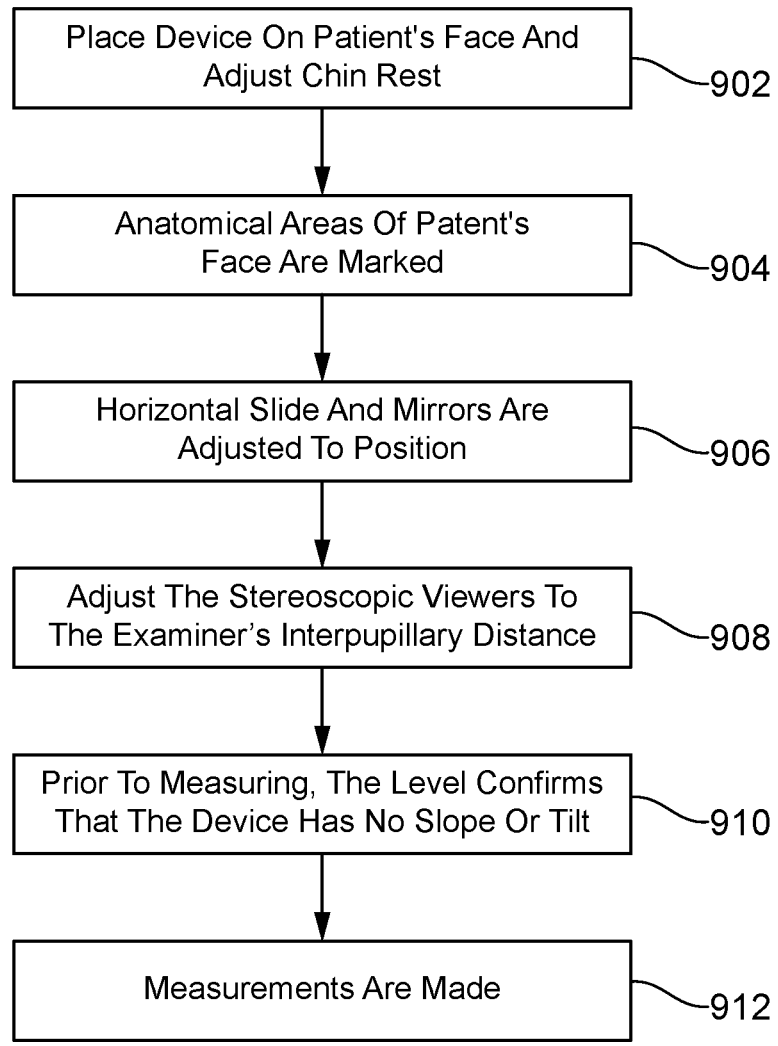
FIG. 9 is a stepwise diagram of a method for measuring anatomical facial features.

Referring now to FIG. 9 a step-wise method diagram showing a method for measuring anatomical features of a patient's face is provided.

At step 902, the anatomical areas of interest are marked with a pen, for instance, if the cheeks are to be measured, a marking pen is used to mark the desired locations of each cheek to be measured.

As step 904, the Examiner places the device onto the patient's face, with the head rest making direct contact on the patient's forehead for a snug fit, and the chin rest is adjusted to fit snugly below the chin.

At step 906, the latching member is loosened to allow the horizontal slide and its attached mirrors to ensure sure the points of interest on each cheek are visible on the mirrors by the Examiner. The mirrors may be tilted to the desired angle, and they can be moved along the length of the slide as desired by the Examiner. However, the location of the mirrors along the slide, the mirrors tilt/angle, and the distance of the mirrors form the patient should all be the same on both sides. The millimeter measurements along the device ensure this.

At step 908, the Examiner adjusts the stereoscopic viewers to the Examiner's interpupillary distance such that the distal ends of the tubes with their accompanying crosses are visible. Both crosses need to be visualized, the left cross by the left eye, and the right cross by the right eye, to ensure that the Examiner remains in midline throughout the entire examination.

At step 910, prior to measuring, a level confirms that the device has no slope or tilt.

At step 912, measurements are performed using one mirror at a time. Using the right mirror first, the Examiner, while remaining in midline, uses his/her right eye only to identify the desired point on the face and measure it on the right mirror using the millimeter grid. In the same fashion, the examiner uses his/her left eye only to measure the point on the left mirror. In order to ensure intra-examiner reliability and to further remain in midline, a detachable telescopic pen is placed between the examiner's nose and the device's knob during the measurement process. This confirms a reliable and reproducible focal point between different sets of measurements by the same examiner.

Advantageously, the device 100 a built-in level to allow the Examiner to keep the instrument as straight as possible for accurate measurement and also made bilateral measurements at the same time. The Examiner will place the device 100 in front of the Examiner's face, making sure the level identifies it as being straight. The mirrors (106 and 108) will allow the Examiner to measure the anterior, superior, posterior and inferior displacement of specific facial anatomic parameter of interest, i.e. the temples, cheeks, globe position, mid-face, nose, jaw, chin, lips, and other parts of the face. Facial asymmetry could be objectively measured before and after an aesthetic or surgical treatment using the device 100.

Preferred embodiments of this invention are described herein, including the best mode known to the inventors for carrying out the invention. It should be understood that the illustrated embodiments are exemplary only and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A device for measuring facial anatomical parameters, the device comprising:
   a vertical bar having a top portion, middle portion, and a bottom portion;
   a horizontal slide adjustably affixed to the vertical bar, wherein the horizontal slide is shaped as an arc having a left portion and a right portion, and wherein the horizontal slide is dimensioned for a face of a patient;
   a forehead positioner pivotably and adjustably affixed to the top portion of the vertical bar, wherein the forehead positioner receives a forehead of the patient;
   a first mirror adjustably affixed to the left portion of the horizontal slide, wherein the first mirror is slidable along the horizontal slide, and wherein the first mirror rotates around its own Y-axis;
   a second mirror adjustably affixed to the right portion of the horizontal slide, wherein the second mirror is slidable along the horizontal slide, and wherein the first mirror rotates around its own Y-axis;
   a measuring grid on or proximate both the first mirror and the second mirror, wherein the measuring grids allows an examiner to accurately measure points of interest of the facial anatomical parameters.

2. The device of claim 1, wherein the horizontal slide is adjustably affixed to the vertical bar using a bracket and a locking mechanism so that the horizontal slide is movable along the vertical bar and is lockable in place.

3. The device of claim 1, further comprising a handle securely affixed to the bottom portion of the vertical bar for enabling the examiner to adjust the device as a whole.

4. The device of claim 1, further comprising a stereoscopic viewer movably affixed to the middle portion of the vertical bar using a movable bracket and a stereoscopic knob, wherein the stereoscopic viewer comprises a pair of eye pieces that adjust to the examiner's interpupillary distance to ensure the examiner remains in a midline position during examination.

5. The device of claim 4, wherein the eye pieces comprise crosshairs disposed on an interior of each eye piece, wherein to remain in midline the examiner sees both crosshairs.

6. The device of claim 1, further comprising a chin bracket adjustably affixed to a lower portion of the vertical bar via a support arm and chin bracket knob, wherein the support arm is movably connected to the vertical bar using an adjustable bracket and the chin bracket knob.

7. The device of claim 1, further comprising:
   a first adjustment member coupled to the first mirror and the horizontal slide, wherein the first adjustment member comprises measurement notches on a top portion thereof to allow the examiner to view a rotational position of the first mirror;
   a second adjustment member coupled to the second mirror and the horizontal slide, wherein the second adjustment member comprises a measurement notches on a top portion thereof to allow the examiner to view a rotational position of the second mirror.

8. The device of claim 7, further comprising:
   a first mirror slide connected to the first adjustment member, wherein the first mirror slide comprises a first aperture;
   a first rotating element connecting the first mirror to a first mirror knob through the aperture to allow the examiner to both rotate the first mirror and slide the first mirror on its z-axis using the first aperture;
   a second mirror slide connected to the second adjustment member, wherein the second mirror slide comprises a second aperture;
   a second rotating element connecting the second mirror with a second mirror knob through the aperture to allow the examiner to both rotate the second mirror and slide the second mirror on its z-axis using the second aperture.

9. The device of claim 1, further comprising a built-in level to allow the examiner to keep the device horizontally aligned to accurately measure the points of interest of the facial anatomic parameters.

10. The device of claim 1, wherein the points of interest comprise anterior, superior, posterior and inferior displacement of specific facial anatomical parameters comprising temples, cheeks, globe position, mid-face, nose, jaw, chin, lips, or any combination thereof.

11. A method for measuring facial anatomical parameters, the method comprising:
  marking anatomical areas of interest of the facial anatomical parameters;
  positioning a vertical bar having a top portion, middle portion, and a bottom portion proximate to the face of a patient, wherein a horizontal slide is adjustably attached to the vertical bar, and wherein the horizontal slide is shaped as an arc having a left portion and a right portion;
  positioning a patient's forehead in a forehead positioner, wherein the forehead positioner is pivotably and adjustably affixed to the top portion of the vertical bar;
  adjusting a first mirror to ensure the anatomical areas of interest on the patient's face is visible in the first mirror;
  adjusting a second mirror to ensure sure the anatomical areas of interest on the patient's face is visible in the second mirror, wherein each of the first and second mirrors are adjustably affixed to the horizontal slide, wherein each of the first and second mirror is slidable along the horizontal slide, and wherein each of the first and second mirror rotates around its own Y-axis;
  taking measurements of the anatomical area of interest.

12. The method of claim 11, further comprising locking the horizontal slide in place using a bracket and a locking mechanism, so that the horizontal slide is movable along the vertical bar and is lockable in place.

13. The method of claim 11, further comprising adjusting the stereoscopic viewer to the examiner's interpupillary distance, wherein the stereoscopic viewer comprises a pair of eye pieces that adjust to the examiner's interpupillary distance to ensure the examiner remains in a midline position during an examination.

14. The method of claim 13, further comprising visualizing a crosshair in each of the eyepieces to further ensure that the examiner remains in the midline position during the examination.

15. The method of claim 13, wherein the stereoscopic viewer is movably affixed to the middle portion of the vertical bar using a movable bracket and a stereoscopic knob.

16. The method of claim 11, further comprising positioning a patient's chin in a chin bracket that is adjustably affixed to a lower portion of the vertical bar using a chin bracket knob via a support arm, wherein the support arm is movably connected to the vertical bar using an adjustable bracket and the chin bracket knob.

17. The method of claim 11, further comprising:
  a first adjustment member coupled to the first mirror and the horizontal slide, wherein the first adjustment member comprises measurement notches on a top portion thereof to allow the examiner to view a rotational position of the first mirror;
  a second adjustment member coupled to the second mirror and the horizontal slide, wherein the second adjustment member comprises a measurement notches on a top portion thereof to allow the examiner to view a rotational position of the second mirror.

18. The method of claim 17, further comprising:
  sliding a first mirror slide connected to the first adjustment member, wherein the first mirror slide comprises an aperture and a first rotating element connecting the first mirror with a first mirror knob through the aperture to allow the examiner to both rotate the first mirror and slide the first mirror on its z-axis;
  sliding a second mirror slide connected to the second adjustment member, wherein the second mirror slide comprises an aperture, wherein the first mirror slide comprises a second rotating element connecting the second mirror with a second mirror knob through the aperture to allow the examiner to both rotate the first mirror and slide the second mirror on its z-axis.

19. The method of claim 11, further comprising leveling the device using a built-in level to allow the examiner to keep the device horizontally aligned to accurately measuring superior, posterior inferior and anterior displacement of facial anatomic parameters.

20. The method of claim 11, wherein the points of interest comprise anterior, superior, posterior and inferior displacement of specific facial anatomic parameter of interest comprising temples, cheeks, globe position, mid-face, nose, jaw, chin, lips, or any combination thereof.

* * * * *